United States Patent (10) Patent No.: US 8,252,230 B2
Benson et al. (45) Date of Patent: Aug. 28, 2012

(54) SYSTEM AND METHOD FOR SANITIZATION

(75) Inventors: Bernard W. Benson, Eden Prairie, MN (US); Thomas E. Birchard, Eagan, MN (US); Matthew S. Nelson, Cottage Grove, MN (US)

(73) Assignee: Hussmann Corporation, Bridgeton, MO (US)

( * ) Notice: Subject to any disclaimer, the term of this patent is extended or adjusted under 35 U.S.C. 154(b) by 305 days.

(21) Appl. No.: 12/777,752

(22) Filed: May 11, 2010

(65) Prior Publication Data

US 2011/0280764 A1 Nov. 17, 2011

(51) Int. Cl.
*A61L 2/16* (2006.01)

(52) U.S. Cl. .............. 422/28; 422/29; 422/292

(58) Field of Classification Search .......... 422/28, 422/29, 292
See application file for complete search history.

(56) References Cited

U.S. PATENT DOCUMENTS

| | | |
|---|---|---|
| 3,286,362 A | 11/1966 | Bolt |
| 3,407,029 A | 10/1968 | Krahe |
| 3,970,426 A | 7/1976 | Stark et al. |
| 4,055,035 A | 10/1977 | Sjostrand et al. |
| 4,073,663 A | 2/1978 | Lundgren |
| 4,255,383 A | 3/1981 | Schenck |
| 4,975,245 A | 12/1990 | Archer et al. |
| 4,992,247 A | 2/1991 | Foti |
| 5,152,968 A | 10/1992 | Foti et al. |
| 5,906,794 A | 5/1999 | Childers |
| 6,276,304 B1 | 8/2001 | Tai |
| 6,767,569 B1 | 7/2004 | Marsden et al. |
| 7,067,089 B2 | 6/2006 | Wen |
| 2003/0047087 A1 | 3/2003 | Phebus et al. |
| 2003/0059507 A1 | 3/2003 | Johnson |
| 2004/0105779 A1 | 6/2004 | Krebs |
| 2005/0053517 A1 | 3/2005 | Finan et al. |
| 2005/0181720 A1 | 8/2005 | Osborn et al. |
| 2005/0186124 A1 | 8/2005 | Fink et al. |
| 2005/0287258 A1 | 12/2005 | Kilburn |
| 2007/0119699 A1 | 5/2007 | Chambers et al. |
| 2007/0140893 A1 | 6/2007 | McVey et al. |
| 2007/0261570 A1 | 11/2007 | Mole |
| 2007/0261712 A1 | 11/2007 | Brandt et al. |
| 2010/0136189 A1* | 6/2010 | Adams et al. ............ 426/335 |

FOREIGN PATENT DOCUMENTS

| | | |
|---|---|---|
| JP | 2001078660 A | 3/2001 |
| JP | 2003514624 A | 4/2003 |

OTHER PUBLICATIONS

International Search Report dated Jan. 30, 2012 of PCT/US2011/035678, filed May 9, 2011.
Written Opinion dated Jan. 30, 2012 of PCT/US2011/035678, filed May 9, 2011.
Chad Company Conveyorized Antimicrobial Spray System (http://www.chadcompany.com/conveyor.htm) Accessed and printed Apr. 20, 2010.

* cited by examiner

*Primary Examiner* — Sean E Conley
(74) *Attorney, Agent, or Firm* — Michael Best & Friedrich LLP

(57) ABSTRACT

A system for sanitizing products on a conveyor including a conveyor for moving products along a direction of conveyance. A first generator and a second generator are each operable to generate airborne sanitizing agents. The first generator includes an outlet configured to discharge at least a portion of the airborne sanitizing agents generated therein across the conveyor in a first direction. The second generator includes an outlet configured to discharge at least a portion of the airborne sanitizing agents generated therein across the conveyor in a second direction. The outlet of the first generator is configured to direct the discharged airborne sanitizing agents toward an inlet of the second generator.

20 Claims, 1 Drawing Sheet

SYSTEM AND METHOD FOR SANITIZATION

BACKGROUND

The present invention relates to a system and method for sanitizing objects along a conveyor. The system may be used to sanitize food products in a food processing line, among other things.

Food processing facilities, especially for meat production, may include an antimicrobial spray system. The system will spray an antimicrobial liquid onto a carcass or meat product as it passes through a designated area along a conveyor chain. The antimicrobial liquid may include lactic acid, and the designated area may include a semi-enclosed cabinet for containing the liquid spray. Such systems are available from CHAD Company of Olathe, Kans.

Furthermore, reaction units for generating reactive oxygen species (ROS) such as $O_3$ (ozone) from oxygen in ambient air are available from AirOCare, Inc. of Rockville, Md. The reaction unit neutralizes airborne contaminants within the reaction unit so that sanitized air (with ozone) is discharged from the reaction unit. The reaction unit can be used in building HVAC systems, grocery store display cases, and food processing environments.

SUMMARY

In one aspect, the invention provides a system for sanitizing products on a conveyor. The system includes a conveyor for moving products along a direction of conveyance. A first generator and a second generator are each operable to generate airborne sanitizing agents. The first generator includes an outlet configured to discharge at least a portion of the airborne sanitizing agents generated therein across the conveyor in a first direction. The second generator includes an outlet configured to discharge at least a portion of the airborne sanitizing agents generated therein across the conveyor in a second direction. The outlet of the first generator is configured to direct the discharged airborne sanitizing agents toward an inlet of the second generator.

In another aspect, the invention provides a system for sanitizing products on a conveyor. The system includes a conveyor for moving products along a direction of conveyance. A first generator is operable to generate airborne sanitizing agents. The first generator has an inlet and an outlet. A second generator is operable to generate airborne sanitizing agents. The second generator has an inlet and an outlet. The outlet of the first generator is configured to direct at least a portion of the airborne sanitizing agents generated by the first generator toward the inlet of the second generator. The outlet of the second generator is configured to direct at least a portion of the airborne sanitizing agents generated by the second generator across the conveyor toward the inlet of the first generator for recirculation.

In yet another aspect, the invention provides a method of applying airborne sanitizing agents to products on a conveyor. Products are moved along a conveyor. Airborne sanitizing agents are generated with a first generator. Airborne sanitizing agents are generated with a second generator. At least a portion of the airborne sanitizing agents generated by the first generator are directed into an inlet of the second generator. At least a portion of the airborne sanitizing agents generated by the second generator are directed across the conveyor into an inlet of the first generator for recirculation.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
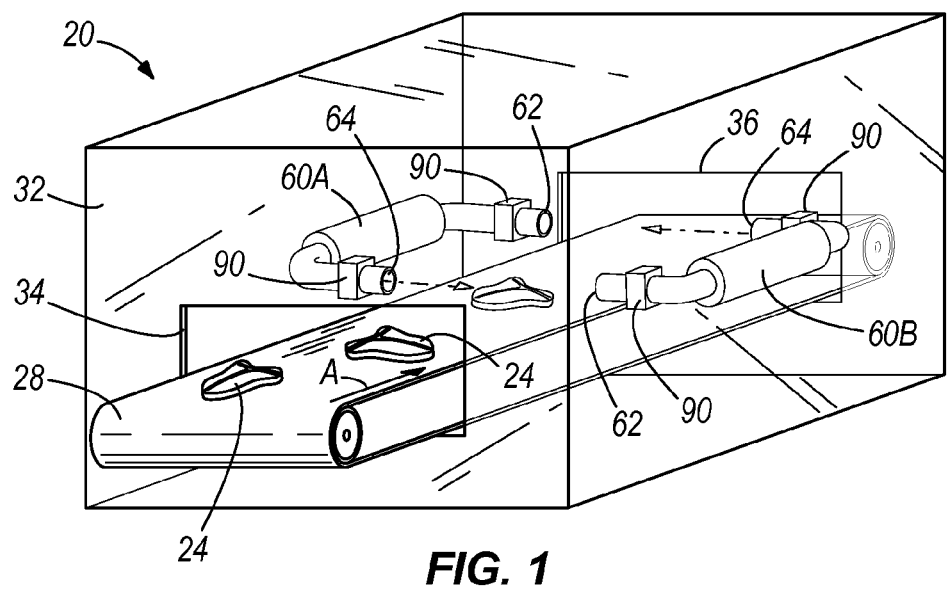
FIG. 1 is a perspective view of a sanitization system according to the present invention.
Figure 2:
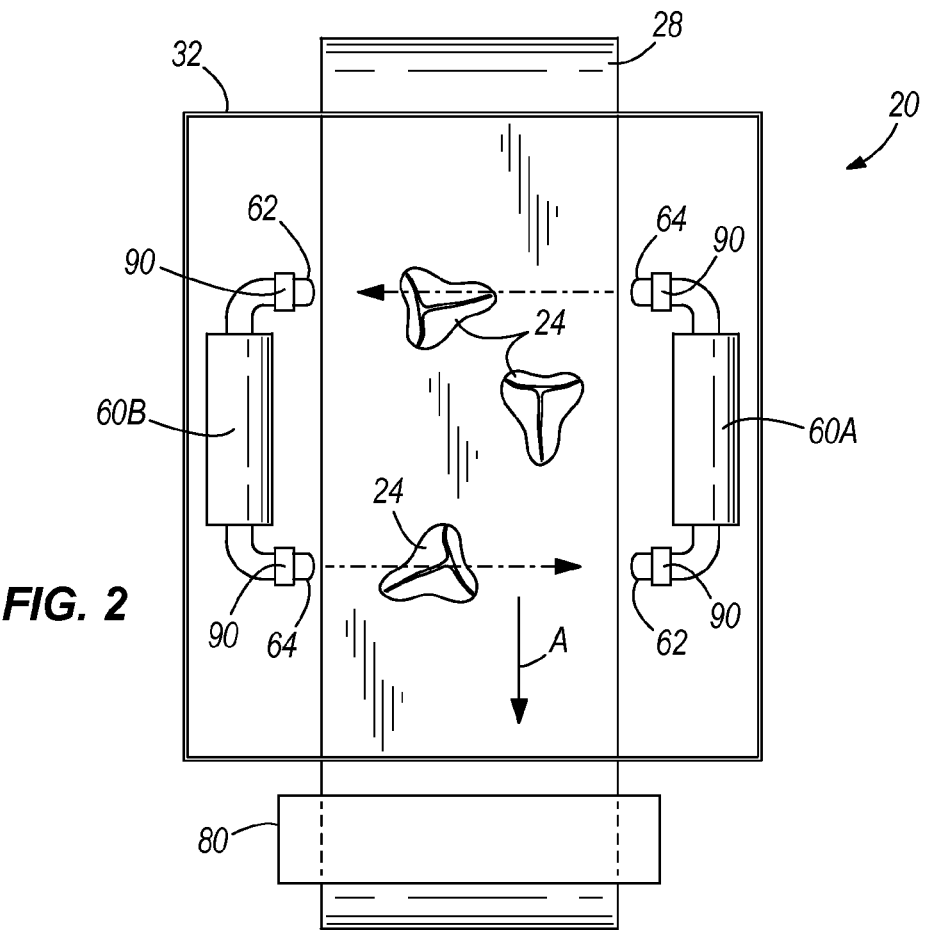
FIG. 2 is a schematic view of the sanitization system of FIG. 1.

FIGS. 1 and 2 illustrate a sanitization system 20 for sanitizing products 24 on a conveyor 28. The products 24 may be food products, such as meat, but the system 20 operates to sanitize the conveyor area regardless of what type of products are conveyed. Although the drawings illustrate a belt-type conveyor 28 on which the products 24 rest, alternate types of conveyors or chains may be substituted, and the products 24 may hang from the conveyor or be supported in other ways besides simply resting thereon. The system 20 described below and illustrated in the figures can be adapted to accommodate different types of conveyors while maintaining many of the features and principles presented in connection with the illustrated construction.

The system 20 may include an enclosure or cabinet 32 defining a substantially enclosed space. The cabinet 32 includes an inlet 34 and an outlet 36 for the conveyor 28 (and the products 24 thereon) to pass into and out of the cabinet 32. The cabinet 32 is otherwise closed on all sides. Although the cabinet 32 is illustrated as being translucent to show the components of the system 20 within the cabinet 32, the cabinet 32 may be constructed of translucent or non-translucent materials, depending upon the needs of the particular system and its environment. For example, the cabinet 32 may be constructed of corrosion resistant, easily cleaned stainless steel for a food processing environment or the like.

As shown in the figures, the system 20 includes two reaction units or "generators" 60A, 60B, each operable to generate reactive oxygen species (ROS) from oxygen, such as naturally occurring $O_2$ present in ambient air. In some constructions, the ROS generators 60A, 60B may be similar to those disclosed in U.S. Patent Publication No. 2007/0119699 of AirOCare, Inc. (Rockville, Md.), although other devices for generating airborne sanitizing agents may be substituted. The entire contents of U.S. Patent Publication No. 2007/0119699 are incorporated by reference herein. As disclosed in U.S. Patent Publication No. 2007/0119699, the ROS generators 60A, 60B are operable to generate one or more ROS, such as singlet oxygen, ozone, atomic oxygen, superoxide, hydrogen peroxide, hydroxyl radical, and peroxynitrite.

In the illustrated construction, the ROS generators 60A, 60B are positioned on laterally opposing sides of the conveyor 28 within the cabinet 32. Each of the ROS generators 60A, 60B includes an inlet 62 and an outlet 64. In the illustrated construction, the inlets 62 (as defined by the direction of airflow passing into the inlets 62) and the outlets 64 (as defined by the direction of airflow discharged from the outlets 64) are substantially perpendicular to a conveyance direction A of the conveyor 28. The inlets 62 and the outlets 64 are also substantially horizontal and thus, parallel to the plane of the conveyor 28, although other arrangements may be constructed. As shown in the figures, the outlet 64 of the first ROS generator 60A is directed toward the inlet 62 of the second ROS generator 60B. In the illustrated construction, the inlet 62 of each one of the ROS generators 60A, 60B is disposed generally across the conveyor from the outlet 64 of the other one of the ROS generators 60A, 60B. Thus, the ROS generators 60A, 60B are configured for recirculation not only by being located within the substantially enclosed space of the chamber 32, but also by the arrangement of the inlets 62 and the outlets 64 as described in further detail below.

Although many of the ROS generated by the ROS generators 60A, 60B have a relatively short half-life and are only or at least predominantly active within the ROS generators 60A, 60B, ozone may be discharged (e.g., forced with a blower or turbine) out of the outlets 64 of the ROS generators 60A, 60B. Thus, each of the ROS generators 60A, 60B is operable to generate a flow of ozone-rich air useful for sanitizing the products 24 on contact.

As the system 20 operates, the products 24 are conveyed on top of the conveyor 24 in the direction A and into the cabinet 32. The ROS generators 60A, 60B operate to discharge airborne sanitizing agents, such as ozone. In the illustrated construction, the first ROS generator 60A discharges ozone-rich air across the conveyor 28 toward the inlet 62 of the second ROS generator 60B so that at least a portion of the ozone-rich air discharged from the outlet 64 of the first ROS generator 60A is received into the inlet 62 of the second ROS generator 60B. This allows the second ROS generator 60B to operate above its rated capacity for ozone production from ambient air since the input to the second ROS generator 60B is already ozone-rich. Furthermore, the second ROS generator 60B discharges ozone-rich air across the conveyor 28 toward the inlet 62 of the first ROS generator 60A so that at least a portion of the ozone-rich air discharged from the outlet 64 of the second ROS generator 60B is received into the inlet 62 of the first ROS generator 60A to define a recirculation loop. Thus, the ozone concentration can build higher and higher until a desired level or a maximum sustainable level is achieved. By locating both the inlets 62 and the outlets 64 of the ROS generators 60A, 60B in the enclosed space, high ozone concentrations can be achieved, and the ozone concentration in the areas surrounding the cabinet 32 may be kept significantly lower and within the federally-mandated limits where personnel are present. The high oxidative gas level may allow for effective (2 log) microbial reduction in 5 feet (5 seconds) in some constructions.

Products 24 conveyed along the conveyor 28 are subjected to a stream of sanitizing, ozone-rich air from the outlet 64 of at least one of the ROS generators 60A, 60B (and both of the outlets 64 in the illustrated construction). The ozone in the air discharged from the ROS generators 60A, 60B has a bacteriostatic or bacteriocidal effect on the products 24 as is known to one of skill in the art, and after passing over the conveyor 28 and the products 24, at least a portion of the ozone-rich airflow from the outlet 64 of each ROS generator 60A, 60B is directly received into the inlet 62 of the other ROS generator 60A, 60B. The illustrated arrangement of the ROS generators 60A, 60B being on opposite sides of the conveyor 28 and discharging ozone-rich air across the conveyor 28 and the products 24 in generally opposite directions assures maximum exposure to the products 24. When referring to the discharge or flow direction of airborne sanitizing agents as "across the conveyor", this means directing the air with the sanitizing agents in a direction that is not parallel to the direction A of conveyance so that the air with the sanitizing agents crosses the space through which products 24 are conveyed. The path of the products 24 may be above the conveyor 24 as in the illustrated construction, but may alternately be below or beside a conveyor.

While the drawings illustrate the cooperating inlets 62 and outlets 64 to be perpendicular to the conveyance direction A and directly opposed to each other to flank the lateral sides of the conveyor 28, alternate arrangements are possible. For example, the outlets 64 may be directed at an inclined angle with the conveyance direction A so as to direct an ozone-rich airflow in a slightly upstream or downstream direction across the conveyor 28 (i.e., either "with" or "against" the flow of products 24). Furthermore, as mentioned briefly above, the ROS generators 60A, 60B may be arranged "in series" (i.e., the first ROS generator 60A discharging directly or at least partially into the second ROS generator 60B) without forming a defined return loop from the second ROS generator 60B back to the first ROS generator 60A. In such a construction, a single flow of ozone-rich air (from the second ROS generator 60B) may be directed across the conveyor 28 and across the products 24, and the ROS generators 60A, 60B may both be positioned on one side of the conveyor 28. The inlet 62 of the first ROS generator 60A may draw in air from an arbitrary location inside the cabinet 32. In such a construction, the system 20 is still operable to build increased ozone concentrations, which remain relatively confined to the cabinet 32.

As shown in FIG. 2, a processing device 80 can be positioned downstream of the ROS generators 60A, 60B in the direction A of conveyor movement. The processing device 80 may be a cutting, grinding, or puncturing device, among other things. In the field of food processing, the processing device 80 can be a meat tenderizer that punctures the conveyed meat products with needles and/or blades. However, the processing device 80 may also be a slicer or any device that, by its operation, inherently risks transporting surface contamination to the inside of the products 24.

In operation, the products 24 pass through the cabinet 32 and are exposed to the ozone-rich environment of the enclosed space, and specifically the ozone-rich airflows of the first and second ROS generators 60A, 60B. The high concentration of ozone to which the products 24 are exposed is effective to sanitize impurities (e.g., neutralize or kill bacteria) present on the outside surfaces of the products 24. Subsequent to the sanitization process, the products 24 can be physically processed (e.g., cut, sliced, punctured, ground, etc.) without risking contamination of the final product from bacteria originally present on the outside of the products 24.

As shown schematically in FIG. 2, a valve 90 may be positioned at the inlet 62 and the outlet 64 of each of the ROS generators 60A, 60B. Each valve 90 is operable to be moved between an open position and a closed position. For example, the valves 90 may be solenoid-operated shut-off valves. In some constructions, the valves 90 may be normally-closed valves. The valves 90 are configured to be open to allow flow through the ROS generators 60A, 60B when the system 20 is operating, and are configured to be closed when the system 20 is not operating. The valves 90 may be controlled automatically by a controller upon start-up and shut-down of the system 20 (e.g., responsive to the conveyor operation or the ROS generator operation) or may be controlled by a system operator. The valves 90 seal the ROS generators 60A, 60B so that the interiors of the ROS generators 60A, 60B are protected from infiltration and potential damage when the system 20, and particularly the surfaces of the conveyor 28 and the interior of the cabinet 32, are sprayed with a liquid cleaning agent that may occur before and/or after working shifts or product runs.

Various features and advantages of the invention are set forth in the following claims.

What is claimed is:

1. A system for sanitizing products on a conveyor, the system comprising:
   a conveyor for moving products along a direction of conveyance;
   a first generator operable to generate airborne sanitizing agents, the first generator having an outlet configured to discharge at least a portion of the airborne sanitizing agents generated therein across the conveyor in a first direction; and
   a second generator operable to generate airborne sanitizing agents, the second generator having an outlet configured to discharge at least a portion of the airborne sanitizing agents generated therein across the conveyor in a second direction,
   wherein the outlet of the first generator is configured to direct the discharged airborne sanitizing agents toward an inlet of the second generator.

2. The system of claim 1, wherein the first and second directions are substantially parallel and opposite.

3. The system of claim 2, wherein the first and second directions are substantially perpendicular to the conveyance direction.

4. The system of claim 1, wherein the outlet of the first generator is oriented at the inlet of the second generator or incrementally upstream of the inlet of the second generator in the conveyance direction.

5. The system of claim 1, wherein the outlet of the second generator is configured to direct airborne sanitizing agents into an inlet of the first generator for recirculation.

6. The system of claim 1, further comprising a cabinet in which the outlets of both the first and second generators, the inlet of the second generator, and at least a portion of the conveyor are substantially enclosed.

7. The system of claim 1, wherein each of the first and second generators is operable to generate reactive oxygen species (ROS) from ambient air.

8. The system of claim 7, wherein each of the first and second generators is operable to generate and discharge ozone ($O_3$).

9. The system of claim 7, wherein the second generator is rated for producing a gaseous output, from ambient air, with a predetermined ROS concentration, the second generator being operable to produce a gaseous output, from an input including at least a portion of the airborne sanitizing agents from the first generator, with an ROS concentration higher than the rated ROS concentration.

10. The system of claim 1, further comprising a processing device configured to carry out at least one of a cutting operation and a grinding operation on food products conveyed along the conveyor, wherein the processing device is positioned downstream of the outlet of at least one of the first and second generators in the direction of conveyance.

11. A system for sanitizing products on a conveyor, the system comprising:
   a conveyor for moving products along a direction of conveyance;
   a first generator operable to generate airborne sanitizing agents, the first generator having an inlet and an outlet; and
   a second generator operable to generate airborne sanitizing agents, the second generator having an inlet and an outlet,
   wherein the outlet of the first generator is configured to direct at least a portion of the airborne sanitizing agents generated by the first generator toward the inlet of the second generator,
   and wherein the outlet of the second generator is configured to direct at least a portion of the airborne sanitizing agents generated by the second generator across the conveyor toward the inlet of the first generator for recirculation.

12. The system of claim 11, wherein the outlet of the first generator is configured to direct at least a portion of the airborne sanitizing agents generated by the first generator across the conveyor toward the inlet of the second generator.

13. The system of claim 12, wherein the outlets of the first and second generators are configured to discharge air sanitizing agents in directions that are oriented parallel to each other and substantially perpendicular to the conveyance direction.

14. The system of claim 11, wherein the outlet of the first generator is oriented at the inlet of the second generator or incrementally upstream of the inlet of the second generator in the conveyance direction.

15. The system of claim 11, further comprising a cabinet in which the inlets and the outlets of both the first and second generators and at least a portion of the conveyor are substantially enclosed.

16. The system of claim 11, wherein each of the first and second generators is operable to generate reactive oxygen species (ROS) from ambient air.

17. The system of claim 16, wherein each of the first and second generators is operable to generate and discharge ozone ($O_3$).

18. The system of claim 16, wherein the second generators is rated for producing a gaseous output, from ambient air, with a predetermined ROS concentration, the second generator being operable to produce a gaseous output, from an input including at least a portion of the airborne sanitizing agents from the first generator, with an ROS concentration higher than the rated ROS concentration.

19. The system of claim 11, further comprising a processing device configured to carry out at least one of a cutting operation and a grinding operation on food products conveyed along the conveyor, wherein the processing device is positioned downstream of the outlet of at least one of the first and second generators in the direction of conveyance.

20. A method of applying airborne sanitizing agents to products on a conveyor, the method comprising:
   moving products along a conveyor;
   generating airborne sanitizing agents with a first generator;
   generating airborne sanitizing agents with a second generator;
   directing at least a portion of the airborne sanitizing agents generated by the first generator into an inlet of the second generator; and
   directing at least a portion of the airborne sanitizing agents generated by the second generator across the conveyor into an inlet of the first generator for recirculation.

* * * * *